United States Patent [19]

Nelson et al.

[11] Patent Number: 4,689,360

[45] Date of Patent: Aug. 25, 1987

[54] OLIGOMERIC MALONATE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[21] Appl. No.: 903,442

[22] Filed: Sep. 4, 1986

Related U.S. Application Data

[63] Continuation-in-part of Ser. No. 786,798, Oct. 11, 1985, abandoned.

[51] Int. Cl.$^4$ .................. C07D 401/12; C07D 401/14; C08K 5/34

[52] U.S. Cl. .................................... 524/102; 524/103; 524/98; 546/19; 546/187; 540/523

[58] Field of Search .................. 546/19, 187; 524/102, 524/103, 98; 540/523

[56] References Cited

U.S. PATENT DOCUMENTS 4,608,436  8/1986  Cantatore et al. .................... 546/19

Primary Examiner—Robert T. Bond
Attorney, Agent, or Firm—Richard A. Rowe

[57] ABSTRACT

Oligomeric derivatives of the dialkyl esters of polyalkyl 1,5-dioxa-9-azaspiro-[5.5]undecane-3,3-dicarboxylic acid are useful light stabilizers for synthetic polymer resins such as polyolefins, and in particular, polypropylene.

15 Claims, No Drawings

OLIGOMERIC MALONATE-BASED LIGHT STABILIZERS FOR PLASTICS

This is a continuation-in-part of co-pending application Ser. No. 786,798 filed on Oct. 11, 1985, now abandoned.

The invention pertains to polymeric compositions which are resistant to degradation when exposed to actinic radiation. In particular, it is directed to resins such as polypropylene stabilized with effective amounts of cyclic acetals of polyalkyl 4-oxopiperidine. The invention is further directed to a novel group of oligomeric malonate based derivatives which are useful as additives for synthetic polymers by acting to retard photo-degradation and to a process for their manufacture.

Many synthetic organic polymers deteriorate rapidly when exposed to sunlight. To circumvent this rapid degradation many additives have been developed to stabilize these resins against the harmful radiation. These additives include hydroxybenzophenones, hydroxybenzotriazoles, organonickel complexes, and a number of compounds which incorporate a hindered amine, such as 2,2,6,6-tetraalkylpiperidine, that is substituted in the 4-position. However, because none of these compounds sufficiently satisfy the stabilization requirements of polymers in their wide variety of forms and applications, there remains a need for new substances which will be more fully satisfactory.

Stable synthetic polymer compositions of the invention are made by their incorporation with of an effective amount of novel acetals derived from a hindered piperidone compound. These compounds may be selected from structures defined by formula I which appears in the Table of Structures, wherein n has a value of 2 to 15, $R^1$ is selected from hydrogen and an alkyl group of 1 to 5 carbon atoms such as methyl, ethyl, n-propyl, n-butyl, n-pentyl but is preferably hydrogen and methyl, and most preferably, hydrogen;

$R^2$ is selected from hydrogen, oxyl, hydroxyl, a straight or branched chain methylene-linked alkyl group from 1 to 18 carbon atoms, such as methyl, ethyl, octyl, octadecyl or 2-ethylhexyl, an alkanoyl group having 2 to 18 carbon atoms, such as acetyl, propanoyl, butanoyl, isopentanoyl, or stearoyl, an alkenyl group of 3 to 4 carbon atoms, an alkenoyl group having 3 to 6 carbon atoms, such as acryloyl, methacryloyl, crotonyl, 2,3-dimethylcrotonyl, an alkynyl group having 3 to 6 carbon atoms such as propanyl or 2-butynyl, a cyanomethyl group, 2,3-epoxypropyl group, an aralkyl group of 7 to 15 carbon atoms such as 3,5-di-tert-butyl-4-hydroxybenzyl, 2-tert-butyl-4-hydroxybenzyl, or 3-tert-butyl-4-hydroxy-5-methylbenzyl, a group —$CH_2CH(OR^5)$—$R^6$, and a group of the formula

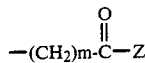

wherein m is either 0 or 1 and Z is a group selected from —$OR^7$; —$N(R^8)(R^9)$ and when m is 0, Z can be a group —$C(O)$—$OR^{10}$ $R^3$ and $R^4$, same or different, are selected from an alkyl group of 1 to 18 carbon atoms such as $R^2$ and hydrogen;

$R^5$ is selected from hydrogen, an aliphatic group of 1 to 18 carbon atoms such as those of $R^2$, an araliphatic group such as benzyl and phenethyl, and an aliphatic acyl group of 2 to 18 carbon atoms such as those of $R^2$;

$R^6$ is selected from hydrogen, an alkyl group of 1 to 16 carbon atoms such as those of $R^2$, and phenyl;

$R^7$ is selected from an alkyl group of 1 to 18 carbon atoms, a cycloalkyl group of 5 to 12 carbon atoms such as cyclopentyl, cyclohexyl, cyclooctyl, and cyclododecyl, allyl, benzyl, phenyl, and a group of formula II wherein $R^1$ and $R^2$ are as described above;

$R^8$ and $R^9$, same of different, are selected from hydrogen, an alkyl group having 1 to 8 carbon atoms such as methyl, ethyl, hexyl, a cycloalkyl group having 5 to 12 carbon atoms such as 4-methylphenyl, 2-methylphenyl, 4-butylphenyl, and aralkyl groups having 7 to 15 carbon atoms such as benzyl, o, m, and p-alkyl-substituted benzyl, and phenethyl, and, $R^8$ and $R^9$ together with the nitrogen atom to which they are attached can form a 5 to 7-membered ring such as pyrrolidine, piperidine and homopiperidine;

$R^{10}$ is selected from an unsubstituted alkyl group of 1 to 18 carbon atoms, phenyl and benzyl and is preferably an alkyl group having 1 or 2 carbon atoms;

p and q, independently, can be either 0 or 1;

X is either —O— or —$NR^{11}$— where $R^{11}$ is selected from hydrogen or an alkyl group of 1 to 8 carbon atoms such as methyl, ethyl, butyl or octyl;

Y is a divalent alkylene group having 2–20 carbon atoms, either straight-chained or branched, wherein the alkylene may be interrupted by —O—, —S— or —$NR^{11}$—, also Y may be selected from a cycloalkylene group of 6-12 carbon atoms such as cyclohexanyl and cyclooctanyl and dialkanylcycloalkane such as dimethanocyclohexane, diethanocyclohexane, dicyclohexanylmethane, dicyclohexanylethane, dimethanocyclohexylmethane, diethanocyclohexylmethane, diethanocyclohexylethane, 2,2-dicyclohexanylpropane, a phenylene group and an aralkylene group having 8 to 19 carbon atoms such as dimethanobenzene and 4,4'-isopropylidenediphenyl and ethano-oxy substituted aralkylene. The oligomers represented by formula I may range in molecular weight from about 650 to 10,000.

The compounds of formula I may be prepared in a multistep process. The first step in the process (n is 1, p and q are 0, X is —O—) is the preparation of the acetal derived from the diol $(HOCH_2)_2C$ $(CO_2R^3)$ $(CO_2R^3)$ with a 4-oxopolyalkylpiperidine of the formula III using a suitable acid catalyst and a suitable solvent as generally known in the art for the preparation of acetals. Examples of suitable acid catalysts are numerous, however, without introducing any limitations are mentioned p-toluenesulfonic acid and methanesulfonic acid. Examples of suitable solvents are cyclohexane and benzene. Although $R^3$ and $R^4$ may be any alkyl group of 1 to 18 carbon atoms for this reaction it is preferred that they be the same and that they be ethyl.

The preparation of the preferred material has been described in the literature, ie., Organic Synthesis Collective Vol. V, 381–383 (1973) and the material is commercially available. This procedure requires reacting diethylmalonate with aqueous formaldehyde in the presence of a catalyst such as potassium bicarbonate and thereafter isolating the product by salting out and solvent extraction.

The reaction of 2,2,6,6-tetraalkyl-4-piperidones with dihydroxy substances to from the corresponding acetal derivatives is well-known and techniques similar to those described in U.S. Pat. Nos. 3,790,525; 3,899,464; 4,007,158; 4,105,626; and EP No. 22,997 may be employed. Of particular interest as a starting component is 2,2,6,6-tetramethyl-4-piperidone. Preparative procedures for this ketone may be found throughout the literature and in U.S. Pat. No. 4,105,626, Column 9. Specifically the compound is prepared by the reaction of ammonia with acetone.

The preparation of other polyalkylpiperidin-4-ones of formula III can be prepared by reaction of ammonia with an aliphatic ketone such as methyl ethyl ketone. This procedure has been described by W. Traube in Chem, Ber. 41,777 (1908).

Compounds of the formula III which carry other alkyl substituents in the 2-position and the 6-position can be prepared in a two step process following the procedures outlined in Helv. Chim. Acta 30,1114(1947) and Monatsh. Chem. 88,464(1957), followed by hydrolysis of the resulting pyrimidine.

The acetalization reaction is generally carried out in a refluxing solution of a water-immiscible solvent at a temperature of about 80° C. in the presence of an acid catalyst. Solvents which work well are cyclohexane and benzene as well as others that may be useful. Acid catalysts which are commonly utilized are organic acids such as methanesulfonic acid, paratoluenesulfonic acid and others which are considered useful.

The acetal resulting from reaction of the diethyl bis(-hydroxymethyl)malonate and and the appropriate piperidin-4-one is generally isolated by solvent extraction and after concentration can be purified by either distillation or crystallization.

The diethyl spiroacetal can be used as a starting material for the second step in the process. Higher molecular weight monomeric esters and amides can be prepared by reaction of the diethyl spiracetal, neat or in solution, with higher molecular weight monofunctional alcohols, amines or mixtures thereof using a basic catalyst like lithium amide or titanium tetraisopropoxide. Oligomers and polymers wherein n is greater than 1 up to a value of about 15 and preferably having a value of 2 to 10 are formed under similar conditions employing difunctional alcohols, amines or mixtures thereof.

The products may be separated from solvent solution and are generally purified by the trituration or crystallization or any other suitable procedure.

The 4-hydroxypolyalkylpiperidines and the 4-aminopolyalkylpiperidines used to convert the acetals into the compounds of the invention are know from German Pat. No. 2,352,658 and U.S. Pat. No. 3,684,765. In general, the 4-hydroxy compounds are prepared from the corresponding 4-oxopiperidines by reduction via catalytic hydrogenation over Raney Nickel and the 4-amino compounds are synthesized via a reductive amination using ammonia or the particular primary amine of interest.

The introduction of an alkyl, alkenyl alkynyl, aralkyl and 2,3-epoxypropyl group can be achieved by reaction of the initially prepared acetal containing the free N—H of the polysubstituted piperidine with suitable halides like methyl iodide, ethyl bromide, propyl bromide, dodecyl chloride, and octadecyl chloride; allyl bromide, methallyl chloride, butenyl chloride, propargyl bromide, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

The introduction of an alkanoyl or an alkenoyl group can be performed by acylation of the parent N—H compound using the suitable acid halide or, when convenient, the acid anhydride. If the acid halide is used the generated hydrogen halide can be scavenged in the same manner as stated previously. Examples of such groups are acetyl chloride, propionyl chloride, hexanoyl chloride, dodecanoyl chloride, octadecanoyl chloride, acetic anhydride, and propionic anhydride. Similarly the oxalyl chloride monoester can be introduced using reagents such oxalyl chloride monomethyl ester and oxalyl chloride monoethyl ester.

For the compounds when $R^2$ is the group —$CH_2CH(OR^5)$—$R^6$ the substituent can be introduced by reaction of the parent N—H compound with the corresponding alkylene oxide such as ethylene oxide, propylene oxide and styrene oxide. The resulting hydroxy compound can be acylated in the manner commonly known in the art using the suitable acid halide and can be alkylated by generating the alkoxide using a base like sodium hydride and treating it with the desired alkyl or aralkyl halide.

When $R^2$ is the group —$(CH_2)_mCOZ$ and m is 0 the appropriate group can be attached by reacting the parent N—H compound with a chloroformate such as methyl chloroformate, ethyl chloroformate, allyl chloroformate, hexyl chloroformate, decyl chloroformate, octadecyl chloroformate, and phenyl chloroformate.

For preparation of the corresponding ureas the parent N—H compound can be treated with the suitable carbamyl halide such as methyl carbamyl chloride, ethyl carbamyl chloride, butyl carbamyl chloride, phenyl carbamyl chloride, dimethyl carbamyl chloride, diethylcarbamyl chloride, dihexylcarbamyl chloride, pyrrolidinyl carbamyl chloride, piperidine carbamyl chloride, and homopiperidine carbamyl chloride. Alternatively, the ureas can be prepared by treating the parent N—H compound with the suitable isocyanate.

Compounds of formula I wherein $R^2$ is the oxyl radical are obtainable from the corresponding N—H compounds by oxidation with a peroxide such as hydrogen peroxide in the presence of a catalyst like sodium tungstate or with percarboxylic acids like metha-chloroperoxybenzoic acid.

When $R^2$ is the group —$(CH_2)_m$—COZ and m is 1 the appropriate group can be attached by reacting the parent N—H compound with an ester of chloroacetic acid such as methyl chloroacetate, ethyl chloroacetate, cyclohexylchloroacetate, ethyl chloroacetate, cyclohexylchloroacetate, benzyl chloroacetate, allyl chloroacetate and phenyl chloroacetate.

The compounds of this invention are effective light stabilizers for synthetic organic polymers.

The following examples are offered to demonstrate but not limit the scope of the invention.

EXAMPLE 1

8,8,10,10-Tetramethyl-1,5-dioxa-9-azaspiro-[5,5]undecane-3,3-dicarboxylic acid, diethylester A mixture of triacetoneamine (25.1 grams, 0.14 mol), diethyl bis(hydroxymethyl)malonate (35.2 grams, 0.16 mol) and paratoluene sulfonic acid (30.4 grams, 0.16 mol) in 360 milliliters of cyclohexane was heated to reflux and the generated water was removed as condensate in a Dean-Stark trap. The mixture was stirred at reflux for 10 hours after which time an additional (17.6 grams 0.08 mol) of malonate was added. After an additional 18 hours at reflux the mixture was cooled to room temperature and the acid neutralized with 300 milliliters of aqueous potassium carbonate (55.2 grams, 0.4 mol). The layers were separated and the aqueous portion was washed with cyclohexane. The combined organic extracts after drying were concentrated under reduced pressure to yield an orange colored viscous liquid (about 52 grams). The crude product was distilled at reduced pressure to yield the above named spiroacetal (44.1 grams, 85%), b.p. 135°–140° C. at 0.15 mm.

Analysis calculated for: $C_{18}H_{31}NO_6$: 60.48% C, 8.74% H, 3.92% N; Found: 60.01% C, 8.78% H, 3.78% N.

In a manner similar to the preparation of Example 1 were prepared:
8,8,9,10,10-Pentamethyl-1,5-dioxa-9-azaspiro-[5.5]undecane-3,3-dicarboxylic acid, diethyl ester
6,9-Diethyl-7,8,10-trimethyl-1,5-dioxa-9-azaspiro-[5.5]undecane-3,3-dicarboxylic acid, diethyl ester.

The 2,6-diethyl-2,3,6-trimethylpiperidin-4-one can be prepared as stated in U.S. Pat. No. 4,105,626, Column 12.

EXAMPLE 2

8,8,10,10-Tetramethyl-1,5-dioxa-9-azaspiro-[5.5]undecane-3,3-dicarboxylic acid, oligomer of 2,2-dimethyl-1,3-propanediol To a mixture of a compound of Example 1 (4.84 gram, 13.5 mmol) and 2,2-dimethyl-1,3-propanediol (1.4 g, 13.5 mmol) which was under a general stream of nitrogen at 150° C. was added lithium amide (60 mg). The temperature was maintained between -5°–155° C. for 18 hours whereupon the mixture was cooled, the viscous residue dissolved in methylene chloride, neutralized with acetic acid, and washed with water. The organic portion was dried and concentrated under reduced pressure to yield a viscous yellow residue. Trituration with petroleum ether (35°–60° C.) yielded an off-white powder, 2.83 grams (56.6%), which sintered at 85° C. Analysis by gel permeation chromatography (GPC) indicates an average molecular weight of approximately 1500–2000 which corresponds to a n value of about 4.0–5.5.

EXAMPLE 3

8,8,10,10-Tetramethyl-1,5-dioxa-9-azaspiro-[5.5]undecane-3,3-dicarboxylic acid, oligomeric with 2-ethyl-2-methyl-1,3-propanediol This compound was prepared in a manner analogous to the preparation of Example 2 with the exception that the reaction time was 2 hours. The product was isolated in greater than 90% yield as a white foam (mp 50°–55° C.). GPC analysis indicated an average molecular weight of about 1200 which corresponds to an n value of about 3.1–3.2.

EXAMPLE 4

8,8,10,10-Tetramethyl-1,5-dioxa-9-azaspiro-[5.5]undecane-3,3-dicarboxylic acid, oligomeric with 2,2-diethyl-1,3-propanediol.

This compound was prepared in a manner analogous to the preparation of Example 2 with the exception that the reaction time was 2 hours. The product was isolated in greater than 90% yield as off-white foam (mp 50°–55° C.). GPC analysis indicated an average molecular weight of about 1200 which corresponds to an n value of about 3.0.

EXAMPLE 5

8,8,10,10-Tetramethyl-1,5-dioxa-9-azaspiro-[5.5]undecane-3,3-dicarboxylic acid, oligomeric with 4,4'-[2-hydroxyethyl]isopropylidenediphenol To a mixture of the compound of Example 1 (3.57 g, 0.01 mmol) and 4,4'-[2,2'-hydroxylethyl]isopropylidenediphenol (3.16 g, 0.01 mmol) under a gentle stream of nitrogen and heated to 150° C. was added lithium amide (50 mg). The mixture was allowed to proceed at about 150° C. for 20 hours before being cooled to ambient temperatures, neutralized with acetic acid, washed with water, dried and concentrated under reduced pressure. The residue was a pale yellow foam weighing 5.15 g (88.6%) and softening point between 53° and 64° C. GPC analysis: average molecular weight is approximately 2500 which corresponds to an n value of about 4.3.

EXAMPLE 6

8,8,10,10-Tetramethyl-1,5-dioxa-9-azaspiro-[5.5]undecane-3,3-dicarboxylic acid, oligomeric condensate with 1,6-hexanediol To a mixture of Example 1 (5.46 g, 15.27 mmol) and 1,6-hexanediol (1.80 g, 15.27 mmol) heated to 100°–110° C. under a stream of nitrogen was added the lithium amide (35 mg) as catalyst. The mixture was allowed to continue with heating for 24 hours before the tacky residue was cooled, dissolved in ether, the catalyst neutralized with acetic acid, and the organic mixture partitioned with water. The organic solution was dried and concentrated to yield a viscous pale yellow material (about 5 g, 85%). Analysis by GPC indicated an average molecular weight of approximately 2000 which corresponds to an n value in formula I of about 5.2.

EXAMPLE 7

8,8,10,10-Pentamethyl-1,5-dioxa-9-azaspiro-[5.5]undecane-3,3-dicarboxylic acid, oligomeric with 2,2-dimethyl-1,3-propanediol A mixture of 8,8,9,10,10-pentamethyl-1,5-dioxa-9-azaspiro-[5.5]undecane-3,3-dicarboxylic acid, diethyl ester (9.69 g, 26.1 mmol), prepared from 1,2,2,6,6-pentamethyl-4-piperidone and diethyl bis(hydroxymethyl) malonate in a manner analogous to that of Example 1 (b.p. 145°–146° C. @0.5 mm), and 2,2-dimethyl-1,3-propanediol (2.71 g, 26.1 mmol) was heated under a gentle stream of nitrogen at 150° C. The catalyst, lithium amide (46 mg, 2.0 mmol), was then added and the reaction was allowed to proceed for 22 h. Upon cooling the mixture was diluted with methylene chloride, the catalyst was destroyed with acetic acid, and the solution was partitioned with water. The organic solution was decolorized, dried and concentrated to yield a white foam (8.10 g). GPC analysis indicated an average molecular weight of about 2000 which corresponds to an n value of about 5.2.

EXAMPLE 8

8,8,10,10-Tetramethyl-1,5-dioxa-9-azaspiro-[5.5]undecane-3,3-dicarboxylic acid, oligomeric with 1,4-cyclohexanedimethanol.

A mixture of the compound of Example 1 (8.73 g, 24.4 mmol) and 1,4-cyclohexanedimethanol (3.52 g, 24.4 mmol) was heated to 100° C. under a nitrogen atmosphere whereupon lithium amide (28 mg) was added. The pressure was reduced to 40 mm Hg and the temperature was increased to 150° C. After one hour the calculated quantity of ethanol had collected in the cold trap. The reaction was cooled and dissolved with methylene chloride (45 ml). Glacial acetic acid was added and the organic solution was washed with water (3×100 ml), dried with sodium sulfate and concentrated to yield a yellow foam (7.72 g, 77%) which melted at 87°–90° C. GPC analysis indicated an average molecular weight of about 1600–1700 which corresponds to an n value of about 3.9 to 4.1.

EXAMPLE 9

8,8,9,10,10-Pentamethyl-1,5-dioxa-9-azaspiro-[5.5]undecane-3,3-dicarboxylic acid, oligomeric with 1,4-cyclohexanedimethanol A mixture of 8,8,9,10,10-pentamethyl-1,5-dioxa-9-azaspiro-[5.5]-undecane-3,3-dicarboxylic acid, diethyl ester, prepared analogously to the compound of Example 1, (8.77 g, 24.0 mmol) and 1,4-cyclohexanedimethanol (3.46 g, 24.0 mmol) was heated to 100° C. under a nitrogen atmosphere and lithium amide (28 mg) was then added. The pressure was then reduced to 65 mm Hg and the temperature was increased to 150° C. The reaction mixture was permitted to proceed for about 2 hours before being cooled and diluted with methylene chloride (50 ml). The mixture was neutralized with acetic acid, was washed with water (3×100 ml) and dried over sodium sulfate. Concentration yielded a white foam (7.22 g, 72%) with a melting point of 88°–90° C. Analysis by GPC indicated an average molecular weight of about 1600–1700 which corresponds to an n value of about 3.8 to 4.0.

EXAMPLE 10

8,8,10,10-Tetramethyl-1,5-dioxa-9-azaspiro-[5.5]undecane-3,3-dicarboxylic acid, oligomeric with 1,4-butanediol A mixture of the compound of Example 1 (10.05 g, 28.1 mmol) and 1,4-butanediol (2.53 g, 28.1 mmol) was heated to 100° C. and lithium amide (33 mg) was then added. The pressure was lowered to 65 mm Hg and the temperature was increased to about 150° C. After 2 hours the mixture was cooled, diluted with methylene chloride and neutralized with acetic acid. The organic solution was washed into water (3×100 ml) dried over sodium sulfate and concentrated to yield a yellow foam. Trituration into ether-petroleum ether (35°–60° C.) yielded the product as an off-white solid (6.55 g, 65.5%) having a melting point of 77°–80° C. GPC analysis of this material indicated an average molecular weight of 1200–1300 which corresponds to an n value of 3.3 to 4.0.

EXAMPLE 11

8,8,10,10-Tetramethyl-1,5-dioxa-9-azaspiro-[5.5]undecane-3,3-dicarboxylic acid, oligomeric amide with 1,6-hexanediamine A mixture of the compound of Example 1 (3.57 parts) and 1,6-hexanediamine (1.18 parts) was heated at 150° C. in the presence of lithium amide and maintained for 18 hours. The crude reaction mixture was cooled, dissolved in methylene chloride and washed with water. The organic solution was dried (sodium sulfate) and concentrated. The product was characterized by NMR spectroscopy.

The spiroacetal derivatives of the invention are particularly useful as light stabilizers for synthetic polymers which undergo degradation in the presence of air and actinic radiation. As used herein polymers are intended to embrace polyolefins including homopolymers of olefins such as low density and high density polyethylene, polypropylene, polystyrene, polybutadiene, polyisoprene and the like; and copolymers of olefins with other ethyleneically unsaturated monomers such as ethylene-propylene copolymer, ethylene-butylene copolymer, ethylene-vinyl acetate copolymer, styrene-butadiene copolymer, acrylonitrile-styrene-butadiene copolymer and the like; polyvinylchlorides and polyvinylidene chlorides including homopolymers of each of vinylchloride and vinylidine chloride, vinylchloride-vinylidene copolymers and copolymers of each vinylchloride and vinylidene chloride with vinyl acetate or other ethylenically unsaturated monomer; polyacetal as such polyoxymethylene and polyoxyethylene; polyesters such as polyethyleneterephthalate; polyamide such as 6-nylon, 6,6-nylon and 6,10-nylon and polyurethanes and polymers derived from α, β-unsaturated acids and derivatives thereof, polyacrylates and polymethacrylates, polyacrylic amides and polyacrylonitrile, as well as copolymers of acrylic acid and one or more of its derivatives with a melamine-formaldehyde resin.

Synthetic polymers have been widely utilized in the art in view of their excellent properties in various forms or shapes, for example, filaments, fibers, yarns, filament sheet, other molded articles and other molded articles made from latex and foam. However, these polymers have some drawbacks such as poor light and heat stabilities among others. Stated illustratively, polyolefins and polyurethane elastomers frequently tend to undergo severe deterioration when exposed to light such as sunlight or ultraviolet light and polyvinyl chloride and polyvinylidine chlorides frequently tend to deterioration when exposed to light such as sunlight or ultraviolet light and polyvinyl chloride and polyvinylidene chlorides frequently tend to deteriorate and become colored by the action of light and heat together with elimination of hydrogen chloride. Polyamides are also frequently subjected to photodegradation. For the purpose of stabilizing these synthetic polymers against such degradation, these have been proposed in the art a number of stabilizers. For example, in the case of polyolefins, benzotriazole and benzophenone compounds; for polyurethanes, phenol compounds and benzophenone compounds; and for polyvinylchlorides and vinylidene chlorides, lead salts such as basic lead silicate and trisilicate, lead maleate and organic tin compounds such as dibutyltinlaurate and dibutyltinmaleate.

The resin should have incorporated within an effective stabilizing amount of a compound described by formula I. The amount will depend upon the nature of the plastic and the amount of radiation to which the plastic will be subject. Generally an amount between about 0.01% and 5.0% by weight of the polymer is effective. Preferably they may be used in concentrations between 0.05 and 1% by weight.

In addition, the light stabilizers of formula I may be used with fillers and additional stabilizers including antioxidants, flame retardant stabilizers, anti-slipping and antistatic agents, supplemental light stabilizers, pigments, dyes, lubricants, etc.

Suitable antioxidants include those of the hindered phenol type such as 2,6-di-t-butyl-p-cresol; 4,4'-bis(2,6-di-t-butylphenol); 4,4'-bis(2,6-diisopropylphenol); 2,4,6-tri-t-butylphenol; 2,2'-thiobis(4-methyl-6-t-butyl-phenol); octadecyl-2(3',5'-di-t-butyl-4'-hydroxyphenyl)-propionate; pentaerythrityl tetrakis(3,5-di-t-butyl-4-hydroxyphenyl-propionate; 1,3,5-tris(3',5'-di-t-butyl-4-hydroxybenzyl) isocyanurate; 1,3,5-tris((3',5'-di-t-butyl-4'-hydroxyphenyl)propionate) isocyanurate; 1,3,5-tris(3',5'-di-t-butyl-4'-hydroxybenzyl)-2,4,6-dimethyl-benzyl)-s-triazine-2,4,6-(1H,3H,5H)-trione and esters of thiodipropionic acid such as dilaurylthiodipropionate and distearylthiodipropionate etc.; hydrocarbyl phosphites such as triphenyl phosphite, trinonyl phosphite, didodecyl pentaerythrityl diphosphite, diphenyldecyl phosphite, tris-(2,4-di-t-butylphenyl)phosphite, bis(2,4-di-t-butylphenyl)pentaerythritol diphosphite, etc. in combinations thereof.

Suitable supplemental light stabilizers include those of the benzotriazole class, such as 2-(2'-hydroxy-5-t-octylphenyl)benzotriazole; 2,(2'-hydroxy-3',5'-di-t-butyl-phenyl)-5-chlorobenzotrialzole; 2-(2'-hydroxy-5'-methylphenyl)benzotriazole; 2-(2'-hydrox-3'-t-butyl-5'-methylphenyl)-5-chlorobenzotriazole; 2-(2'-hydroxy-3',5'-di-t-amylphenyl)-benzotriazole; those of the hydroxybenzophenone type such as 2-hydroxy-4-methoxybenzophenone; 2-hydroxy-4-octyloxybenzophenone; 2,2'-dihydroxy-4,4'-di-methoxybenzophenone; hindered phenol esters, such as n-hexadecyl-3,5-di-t-butyl-4-hydroxybenzoate; and 2',4'-di-t-butylphenol-3, 5-di-t-butyl-4-hdyroxybenzoate; metal complexes such as nickel complexes of 2,2'-thiobis-(4-6-octylphenol), nickel butylamine complexes of 2,2'-thiobis(4-t-octylphenol); nickel dibutyl thiocarbamate; nickel salts of 4-hydroxy-3,5-di-t-butylbenzylphosphonic acid mono-alkyl esters where alkyl is methyl, ethyl, propyl, butyl etc.; nickel complexes of to 2-hydroxy-4-methylphenyl undecylketoneoxime. Further illustrative examples of suitable antioxidants of supplemental light stabilizers can be found in columns 3 and 4 of U.S. Pat. Nos. 3,488,290 and 3,496,134.

EXAMPLE 12–19

In order to further illustrate the effectiveness of the above-described compounds as light stabilizers the previously described materials of Examples 2-5, and 7-10 were each incorporated into a commercially available polypropylene resin manufactured by Hercules Corporation as PRO-FAX ® 6301 Polypropylene Resin. The light stabilizers were incorporated with the polypropylene by solvent blending (methylene chloride) at concentrations of 0.25% by weight of the total resin composition and as a primary antioxidant stearyl beta-3,5-di-t-butyl-4-hydroxyphenylpropionate was used at a concentration of 0.2%. The resin was then extruded at 200° C. and compression molded at 6,000 psi at 188° C. to produce films having thicknesses of 5 mils. A control film was produced by an identical procedure with the light stabilizer omitted. Each film was exposed to Xenon Arc in an Atlas Weather-o-meter until the infrared carbonyl absorption increased by 0.5, which is considered to be the failure point.

TABLE I

| Example No. | Stabilizer | Hours to Failure |
|---|---|---|
|  | Control | 300 |
| 12 | Example 2 | 3050 |
| 13 | Example 3 | >2500 |
| 14 | Example 4 | >2500 |
| 15 | Example 5 | 2100 |
| 16 | Example 7 | >2500 |
| 17 | Example 8 | >2000 |
| 18 | Example 9 | >2000 |
| 19 | Example 10 | >2000 |

TABLE OF STRUCTURES

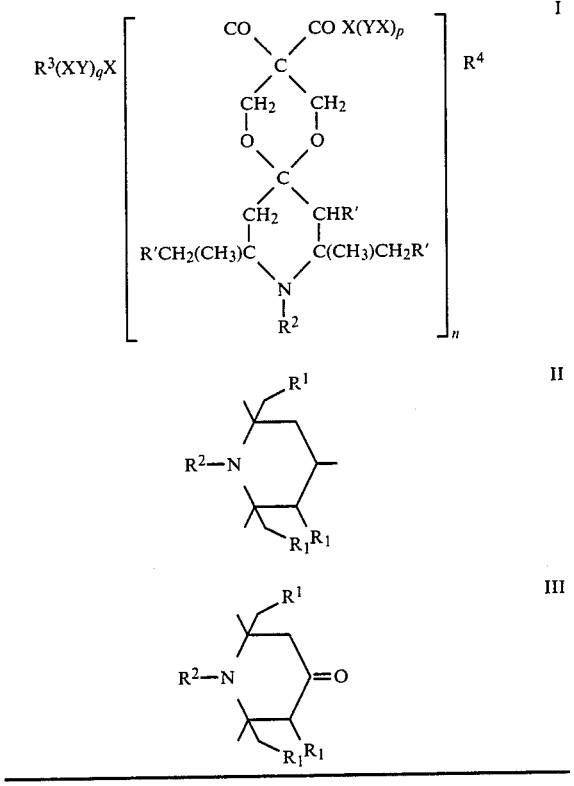

What is claimed is:

1. An oligomer of the formula I wherein n has a value of 2 to 15 and $R^1$ is selected from hydrogen and an alkyl group of 1 to 5 carbon atoms, $R^2$ is selected from hydrogen, oxyl, hydroxyl, a straight or branched chain methylene-linked alkyl group from 1 to 18 carbon atoms, an alkanoyl group having 2 to 18 carbon atoms, an alkenyl group of 3 to 4 carbon atoms, an alkenoyl group having 3 to 6 carbon atoms, an alkynyl group having 3 to 6 carbon atoms, a cyanomethyl group, a 2,3-epoxy propyl group, an aralkyl group of 7 to 15 carbon atoms, a group —$CH_2CH(OR^5)$—$R^6$, and a group of the formula —$(CH_2)_mC(O)$—Z where m is either 1 or 0 and Z is a group selected from —$OR^7$, —$N(R^8)(R^9)$ and —$C(O)$—$OR^{10}$;

$R^3$ and $R^4$, same or different, are is selected from an alkyl group of 1 to 18 carbon atoms and hydrogen;

$R^5$ is selected from hydrogen, a straight or branched chain methylene-linked alkyl group from 1 to 18 carbon atoms, an alkanoyl group having 2 to 18 carbon atoms, an alkenyl group of 3 to 4 carbon atoms, an alkenoyl group having 3 to 6 carbon atoms, a cyanomethyl group, a 2,3-epoxy propyl group, an aralkyl group of 7 to 15 carbon atoms, $R^6$ is selected from hydrogen, an alkyl group of 1 to 16 carbon atoms and phenyl;

$R^7$ is selected from an alkyl group of 1 to 18 carbon atoms, a cycloalkyl group of 5 to 12 carbon atoms, allyl, benzyl, phenyl, and a group of formula II wherein $R^1$ and $R^2$ are as described above;

$R^8$ and $R^9$, same or different, are selected from hydrogen, an alkyl group having 1 to 8 carbon atoms, a cycloalkyl group having 5 to 12 carbon atoms such as those of $R^7$, an aryl group having 6 to 10 carbon atoms, and an aralkyl group having 7 to 15 carbon atoms; $R^8$ and $R^9$ may also, together with the nitrogen atom to which they are attached, form a 5 to 7-membered ring selected from the group consisting of pyrrolidine, piperidine, and homopiperidine;

$R^{10}$ is selected from an alkyl group of 1 to 18 carbon atoms, phenyl and benzyl;

p and q, independently, may be either 1 or 0;

X is either —O— or —$NR^{11}$— where $R^{11}$ is selected from hydrogen or an alkyl group of 1 to 8 carbon atoms; and Y is selected from a divalent alkylene group having 2 to 20 carbon atoms, either straight-chained or branched, wherein the alkylene may be interrupted by —O—, —S— or —$NR^{11}$—, a cycloalkylene group of 6-12 carbon, a dialkanylcyclohexane, a phenylene group, an aralkylene group having 8 to 19 carbon atoms, and an ethano-oxy substituted aralkylene group, wherein said formulas are:

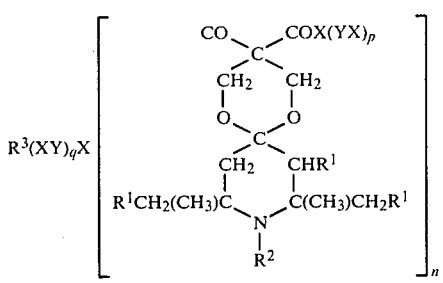

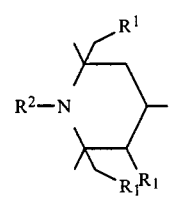

2. A compound of claim 1 wherein $R^1$ is hydrogen and X is —O—.

3. A compound of claim 2 wherein p is 1 and q is 1 or 0.

4. A compound of claim 2 wherein n has a value between 3 and 8, p is 1 and q is 1 or 0.

5. A compound of claim 4 wherein Y is the 2,2-dimethyl-1,3-propylene group and $R^2$ is hydrogen.

6. A compound of claim 4 wherein Y is the 2-ethyl-2-methyl-1,3-propylene group and $R^2$ is hydrogen.

7. A compound of claim 4 wherein Y is the 2,2-diethyl-1,3-propylene group and $R^2$ is hydrogen.

8. A compound of claim 4 wherein Y is the 2,2-dimethyl-1,3-propylene group and $R^2$ is methyl.

9. A compound of claim 4 wherein Y is the 1,4-dimethanocyclohexanyl group and $R^2$ is hydrogen.

10. A compound of claim 4 wherein Y is the 1,4-dimethanocyclohexanyl group and $R^2$ is methyl.

11. A compound of claim 4 wherein Y is the 1,4-butylene group and $R^2$ is hydrogen.

12. A compound of claim 4 wherein Y is 4,4'-diethanoisopropylidene diphenol and $R^2$ is hydrogen.

13. A synthetic polymer composition stabilized against light induced deterioration comprising an organic polymer normally subjected to deterioration by light, and from 0.01-5% by weight of a compound of the general formula of claim 1.

14. A composition of claim 13 wherein the organic polymer is a polyolefin homopolymer or copolymer.

15. A composition of claim 14 wherein said organic polymer is a homo or copolymer of polypropylene.

* * * * *